United States Patent
Cha et al.

(10) Patent No.: US 6,964,734 B2
(45) Date of Patent: Nov. 15, 2005

(54) PLANAR REFERENCE ELECTRODE

(75) Inventors: Geun Sig Cha, Seoul (KR); Gang Cui, Yeongil-si (KR); Jina Yoo, Seoul (KR); Joung Su Lee, Seoul (KR); Hakhyun Nam, Seoul (KR)

(73) Assignee: Geun Sig Cha, Seoul (KR)

( * ) Notice: Subject to any disclaimer, the term of this patent is extended or adjusted under 35 U.S.C. 154(b) by 0 days.

(21) Appl. No.: 09/818,750

(22) Filed: Mar. 27, 2001

(65) Prior Publication Data

US 2001/0032785 A1 Oct. 25, 2001

(30) Foreign Application Priority Data

Mar. 27, 2000 (KR) ........................................ 2000-15470

(51) Int. Cl.[7] ............................................ G01N 27/30
(52) U.S. Cl. ......................................... 204/435; 427/58
(58) Field of Search ............................ 204/435; 427/58

(56) References Cited

U.S. PATENT DOCUMENTS

| | | | |
|---|---|---|---|
| 2,846,386 A | * | 8/1958 | Ingruber |
| 3,264,205 A | * | 8/1966 | Leonard et al. |
| 3,461,055 A | * | 8/1969 | Staunton |
| 3,498,899 A | * | 3/1970 | Kater et al. |
| 3,575,834 A | * | 4/1971 | Hoole et al. |
| 4,002,547 A | * | 1/1977 | Neti et al. |
| 4,031,606 A | * | 6/1977 | Szonntagh |
| 4,162,211 A | * | 7/1979 | Jerrold Jones |
| 4,252,124 A | * | 2/1981 | Maurer et al. |
| 4,714,527 A | * | 12/1987 | Hofmeier et al. |
| 4,857,166 A | * | 8/1989 | Kotani |
| 4,933,048 A | | 6/1990 | Lauks |
| 5,152,882 A | * | 10/1992 | Benton |
| 5,421,983 A | * | 6/1995 | Slack et al. |
| 5,554,272 A | * | 9/1996 | Benco et al. |

OTHER PUBLICATIONS

An article entitled Miniaturized Reference Electrode Based on a Perchlorate–Selective Field Effect Transistor, By Wilhelm Potter et al., published by Analytical Chemistry, vol. 67, No. 24, Dec. 15, 1995, pp. 4586–4588.

An article entitled Thick Film Silver–Silver Chloride Reference Electrodes, By A.W.J Cranny et al., published by Meas. Sci. Technol. 9 (1998) pp. 1557–1565. Printed in the UK.

An article entitled Promising New Solid–State Reference Electrode, By K. Nagy et al., published by J. electrochem. Soc., vol. 144, No. 1, Jan. 1997.

An article entitled Disposable Reference Electrode, By A. Mroz et al., published by Analyst, Jun. 1998, vol. 123 pp. 1373–1376.

An article entitled Development of Thin–Film Liquid–Junction AG/AGCL Reference Electrodes and Their Application to One–Chip Micro Chemical Sensors, By H. Suzuki et al., published by Transducers Jun. 7–10, 1999, pp. 1180–1183.

\* cited by examiner

*Primary Examiner*—Kaj K. Olsen
(74) *Attorney, Agent, or Firm*—Bachman & LaPointe, P.C.

(57) ABSTRACT

The present invention disclose a method for fabricating planar reference electrodes. Particularly, the present invention relates to the planar reference electrode comprising plate (4); electrode connection (1); electrode (3); insulating membrane (2); inner reference solution (5); junction (7 or 9); and protecting membrane (6, 8 or 9), and processes for fabrication thereof, in which the junction is composed of porous material such as cotton thread, glass fiber, cellulose nitrate, cellulose acetate, filter paper and any material that can produce capillary action; porous polymer membrane; or a capillary either directly printed on the substrate or inserted with a thin film. The planar reference electrode of the present invention exhibit stable electric potential and short activation period, and may be used in both potentiometry and voltammetry. The planar reference electrodes of the present invention can be easily miniaturized and mass produced.

12 Claims, 10 Drawing Sheets

PLANAR REFERENCE ELECTRODE

FIELD OF THE INVENTION

The present invention relates to a planar reference electrode and a process for fabrication thereof and more specifically to the reference electrode including substrate (4); electrode connection part (1); electrodes formed on the plate (3); insulating membrane (2); inner reference solution (5); junction (7 or 9); and protecting membrane (6, 8 or 9), in which the junction comprises porous material such as cotton thread, glass fiber, cellulose nitrate, cellulose acetate, filter paper; polymer-based porous membrane; or capillary type.

BACKGROUND OF THE INVENTION

Electrochemical methods such as potentiometry or voltammetry have been commonly applied in the analytical laboratories to determine specific chemical components contained in clinical, environmental or industrial samples. However, the samples collected from remote sampling sites often require special pretreatment to prevent them from contamination or degradation during transportation to the laboratories. The laboratory-based instruments is expensive to operate, and should be managed by the technicians specially trained in the area. In addition to the aforementioned problems, some clinical samples, e.g., blood for in vitro tests, would be collected in smaller volume in order to reduce the patient's uncomfortable feelings and shock. For these reasons, on-spot-monitoring or point-of-care-testing (POCT) with convenient and economic hand-held devices is becoming popular to expedite the analytical tasks, while reducing the laboratory operational costs and errors by non-specialists.

To design portable electroanalytical devices, miniaturization of the electrochemical sensor system including reference and working electrodes should be attained. Numerous schemes have been proposed to accomplish miniaturized working electrodes, and many of them are now commercially available, while reference electrodes have not been extensively developed for miniaturization thereof.

An ideal miniaturized reference electrode requires several characteristics, such as insensitive response to the sample's composition change, providing a constant potential which is characteristic of a reversible redox couple reaction within the half cell. The reversibility of a fast redox reaction ensures the recovery of the same potential even after the passage of electric currents through the reference cell. The reference cell including insoluble metal salt (e.g., Ag/AgCl) provides constant potential by exchanging a cation or anion which is normally contained in a high concentration of reference electrolyte, either in aqueous solution or in a hydrogel medium, which is in contact with the sample solution through a junction. Accordingly, when such a reference system is miniaturized, it is necessary to implement a micro junction, easily activated reference electrolyte, and stable insoluble metal salt on a chip. To use the miniaturized reference electrode for an electrochemical POCT system, fast stabilization of the potential and reproducibility are prerequisite.

Several types of miniaturized reference electrodes have been proposed previously. A reference electrode comprising a screen printed silver/silver chloride electrode, a layer of low temperature melting glass paste or a silicone polymer paste containing potassium chloride, and a hydrophobic polymer membrane that can form micro junctions by hydration has been reported (Cranny, A. W. J.; Atkinson, J. K., Meas. Sci. Technol. 1998, 9, 1557–1565). Unfortunately, the presoaking time for this reference system takes more than an hour and the potential is unstable, although it provides long operational lifetime. Another example of small reference electrode was prepared by the following steps: placing an inner reference electrolyte in the form of hydrogel on a silver/silver chloride electrode; and covering the hydrogel layer with a hydrophobic polymer membrane with a small opening (Lauks, I. R., U.S. Pat. No. 4,993,048). This reference electrode system provides a constant potential only for a short period of time (a few minute) as the small volume of inner reference electrolyte depletes into the sample solution through the junction, and changes the inner salt concentration. However, the formation of a small exposure, which is typically a few micrometers, in the process of mounting an outer membrane is not easy and often results in malfunction of the reference electrode system due to the sealed pore. In addition, there is a possibility that large particulates contained in sample may block the junction. Such an abnormality can not be predicted in advance and lowers the reliability of the measurement. Miniaturized reference electrodes based on field effect transistor (FET) were also proposed (Potter, W.; Dumschat, C.; Cammann, K., Anal. Chem., 1995, 67, 4586–4588): the top of the ion-selective layer is coated with another layer containing solid potassium perchlorate. Since potassium perchlorate is not readily soluble in aqueous solutions, the perchlorate activity in the aqueous surface layer is equal to that of a saturated solution and leads to a constant potential. However, to deposit the potassium perchlorate layer, this system requires a well (diameter 2 mm, and height 1.5 mm) affixed on the chip and is not suitable for mass fabrication.

In order to develop planar reference electrodes that are suitable for mass fabrication with stable reference potential for an elongated period of time, porous material such as cotton thread, glass fiber, cellulose nitrate, cellulose acetate, filter paper and any material that can induce capillary action; porous polymer membrane; or viscous inner reference solution enclosed in a well formed with a punched film layer has been provided as the junction of the reference electrode. The present invention discloses that the aforementioned reference electrodes maintain stable potentials and provide a relatively short activation period. Hence, it can be employed both in potentiometry and voltammetry. The reference electrodes proposed in this invention can be easily miniaturized in planar structure and appropriate for mass fabrication.

SUMMARY OF THE INVENTION

The present invention describes a miniaturized planar-type reference electrodes that can be used both in potentiometry and voltammetry and a method for fabricating it. Further objectives and advantages of the present invention will appear hereinafter.

BRIEF DESCRIPTION OF THE DRAWINGS

Features and advantages of the present invention may be understood more clearly from the following detailed description in conjunction with the accompanying drawings, in which;

FIG. 1b shows the inner structure of FIG. 1a.

FIG. 2b shows the internal structure of FIG. 2a.

a: Ag/AgCl electrode screen printed on a polyester substrate b: Ag/AgCl electrode screen printed on polycarbonate substrate

DRAWING REFERENCE NUMERALS

Figure 1A:
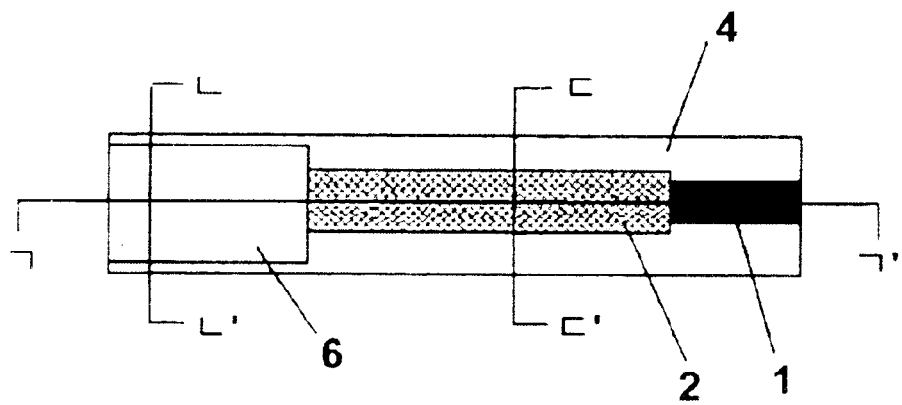
FIG. 1a shows the front view of the planar reference electrode of the present invention in which the junction comprises porous substance or a capillary formed on the substrate.
Figure 1B:
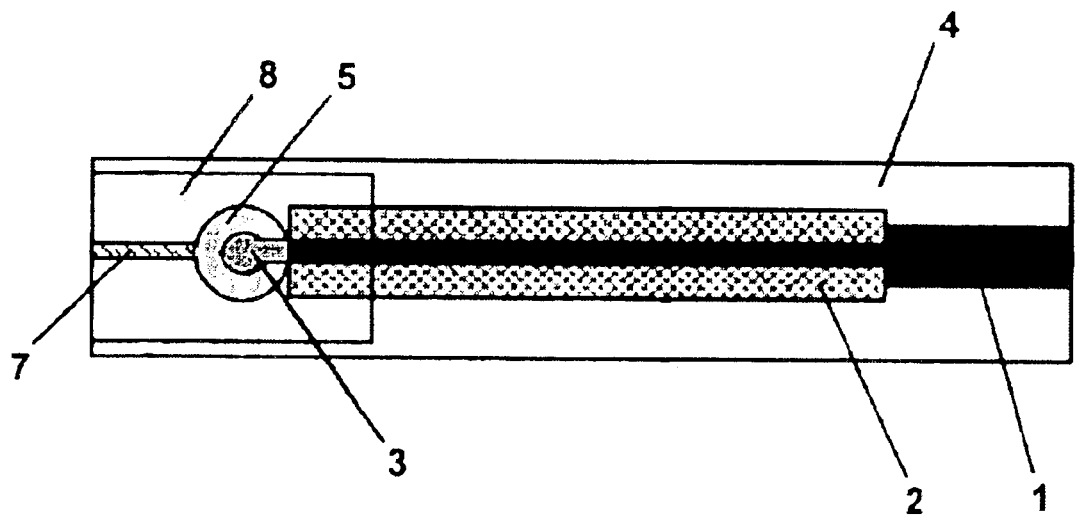
Figure 1C:
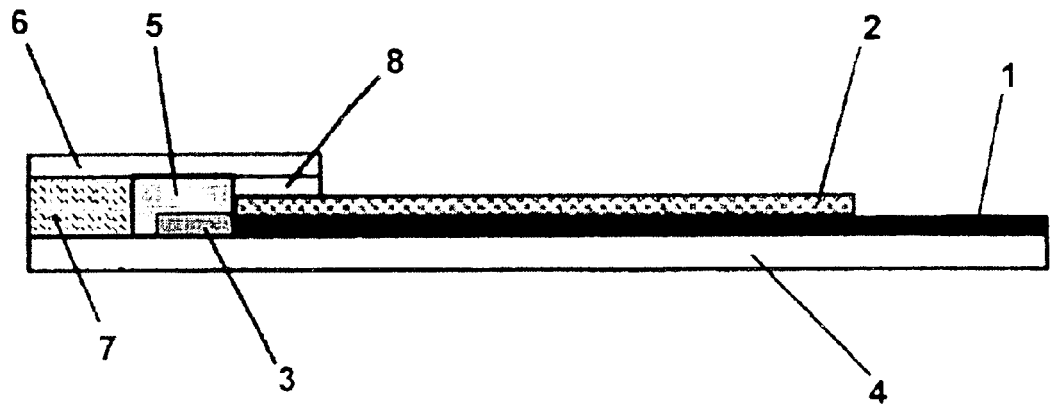
FIG. 1c shows the cross sectional view of FIG. 1a through A–A' line.
Figure 1D:
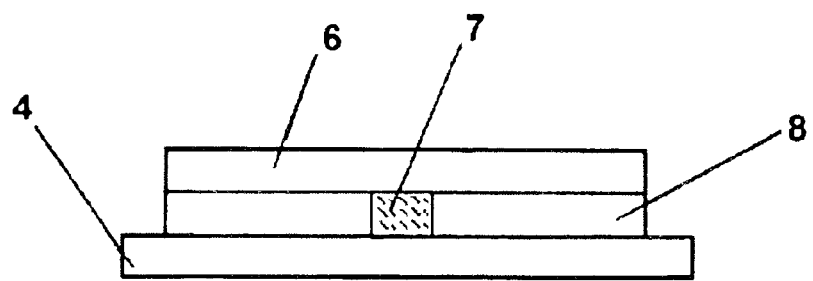
FIG. 1d shows the cross sectional view of FIG. 1a through B–B' line.
Figure 1E:
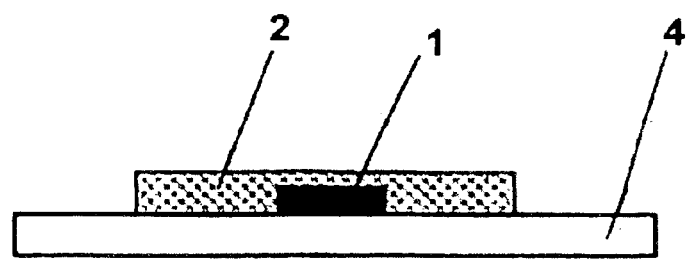
FIG. 1e shows the cross sectional view of FIG. 1a through C–C' line.
Figure 2A:
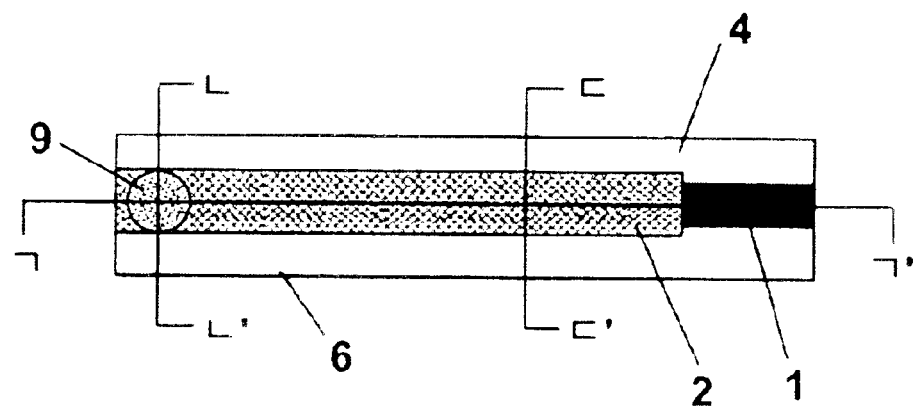
FIG. 2a shows the front view of the planar reference electrode of the present invention, in which the junction comprises porous polymer membrane.
Figure 2B:
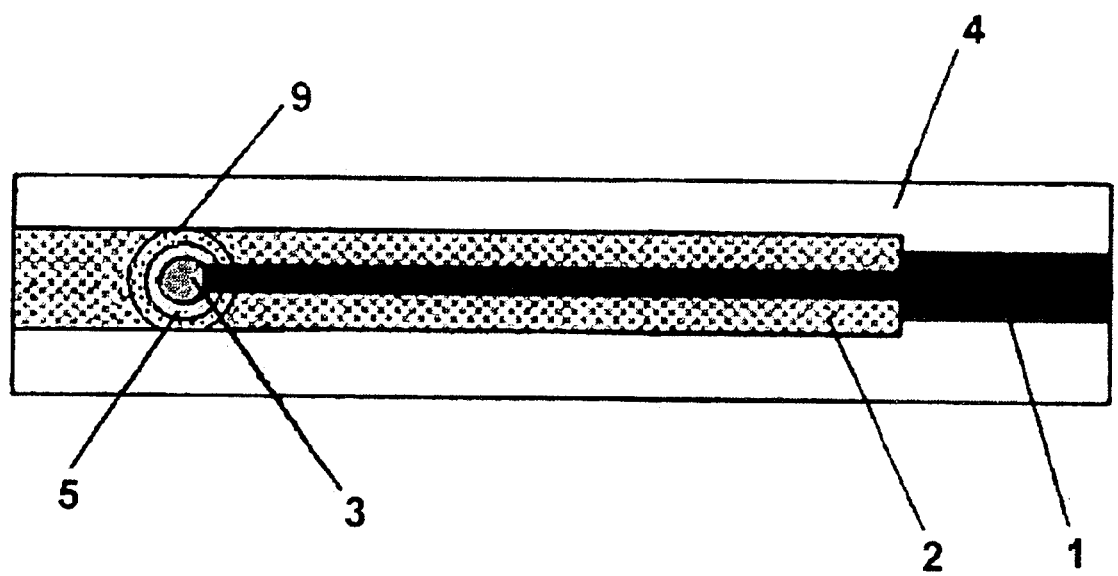
Figure 2C:
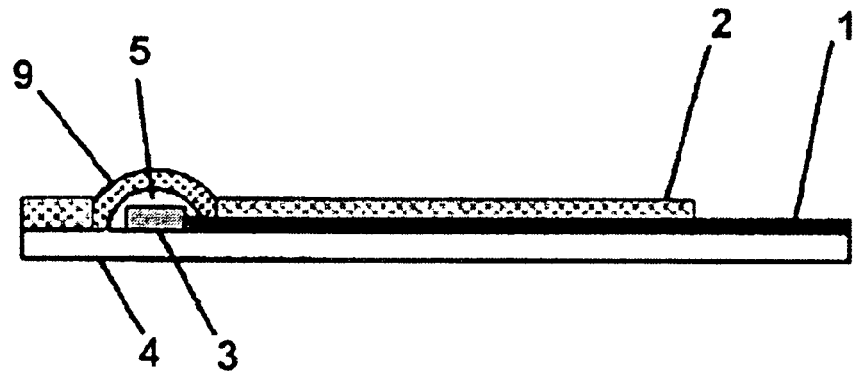
FIG. 2c shows the cross sectional view of FIG. 2a through A–A' line.
Figure 2D:
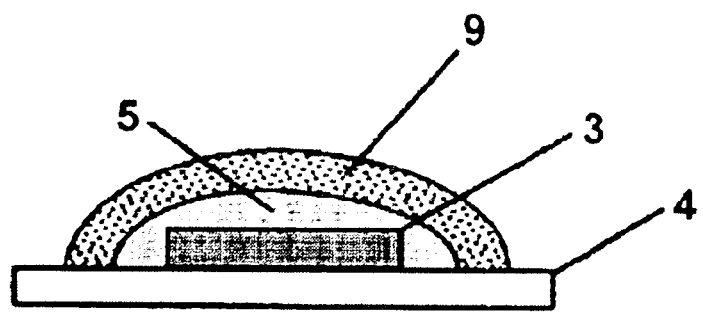
FIG. 2d shows the cross sectional view of FIG. 2a through B–B' line.
Figure 2E:
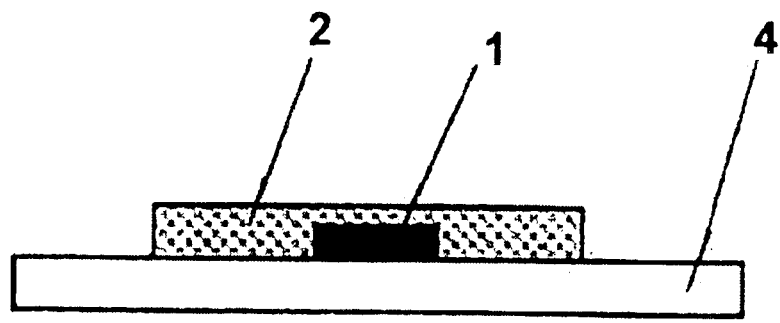
FIG. 2e shows the cross sectional view of FIG. 2a through C–C' line.

1: electrode connection part
2: insulating membrane
3: electrode
4: substrate
5: inner reference solution
6, 8: protection membrane 7: junction 9: porous polymer membrane (functions as both junction and protection membrane)

DETAILED DESCRIPTION OF PREFERRED EMBODIMENTS

In accordance with the present invention, the object of the present invention could be accomplished by providing reference electrode including plate (4); electrode connection part (1); electrode (3); insulating membrane (2); inner reference solution (5); junction (7 or 9); and protecting membrane (6, 8 or 9), wherein the junction comprises porous material such as cotton thread, glass fiber, cellulose nitrate, cellulose acetate, filter paper and any material that can produce capillary action; porous polymer membrane; or a film with micro capillary.

FIGS. 1a, 1b, 1c, 1d, 1e, 2a, 2b, 2c, 2d and 2e show the examples of the planar reference electrode of the present invention. FIGS. 1a, 1b, 1c, 1d and 1e show the examples of the planar reference electrode in which junction is composed of porous substance or a film with a line of micro capillary. FIGS. 2a, 2b, 2c, 2d and 2e show the examples of the planar reference electrode in which junction is composed of porous polymer membrane. As depicted in FIGS. 2a, 2b, 2c, 2d and 2e, an extra protection membrane is not needed since the porous polymer membrane itself also plays a role of a protection membrane when porous polymer membrane is used as a junction.

The planar reference electrode of the present invention is characterized in that the junction is composed of porous substance such as cotton thread, glass fiber, cellulose nitrate, cellulose acetate, filter paper and any other material that can provide capillary action; porous polymer membrane; or a film with a line of micro capillary.

The junction plays a role in transferring ions through the micro channels between sample solution to be tested and the inner reference solution, thereby the two solutions is electrically connected. On the other hand, the junction must not corrupt the sample solution or inner reference solution by moving inner reference solution toward the outside sample solution and vice versa.

The junction of the present invention comprises porous material, porous polymer membrane or capillary. If a micro capillary formed on a thin film is used as the junction, the performance of the reference electrode is not dependent on the type of junction-forming material employed.

The planar reference electrode of the present invention improves the stability of electrode potential and reduces the activation period of the electrode by using the aforementioned junction-forming methods and materials. Advantageously, the reference electrode having porous polymer membrane as a junction has shorter hydration period than other reference electrodes that employ hydrophobic outer membrane. One of the preferred porous polymer material is cellulose nitrate. In addition, the reference electrode with micro capillary provide faster activation time since the junction needs not to be hydrated. Such a electrode can be prepared conveniently due to simplicity of the junction-forming method.

The inner reference solution (5) comprises hydrogel containing electrolytes which is composed of 85–99% weight % of glycerol solution; 1–10 weight % of agar solution; polymer glue; or other water soluble polymers.

The inner reference solution of the present invention exploits a viscous solution or a soluble polymer containing a high concentration of electrolytes. Since the inner reference solution is made of the viscous solution, the inner reference solution need not be hydrated and provide rapid activation while minimizing the contamination of sample solution due in part to the retarded diffusion of inner reference electrolytes. The activation time of the reference electrode can be reduced further by adding hygroscopic substance such as $CaCl_2$ with a proper concentration when hydrogel is used as an inner reference solution.

As a soluble polymer forming hydrogel, poly(vinyl pyrrolidone) (PVP) is preferable. The hydrogel can be prepared by dissolving soluble polymer with organic solvent and drying.

As an electrolyte, silver nitrate or perchloric acid is preferred, if silver is used as an electrode material, KCl or NaCl is preferred, if Ag/AgCl is used, NaOH or KOH is preferred, if mercury/mercury oxide is used.

The plate (4) is formed of alumina, glass plate or thermostable plastic substance, preferably polyester or polycarbonate. Polycarbonate is favored as the plate material in the present invention if the cellulose nitrate is used as the outer membrane component.

The protection membrane (6, 8 or 9) is formed of plastic substance including polyester or porous polymer membrane as cellulose nitrate.

Porous polymer such as cellulose nitrate has micelle structure, uniform porosity and hydrophilic property. Advantageously, it can be exploited not only as protection membrane and but also as polymer membrane type junction in the reference electrode of the present invention.

The electrode (3) can consist of metal layer such as Ag, Pd, Cu, Pt and any conducting material. Also, the electrode can consist of metal layer/insoluble metal layer such as Ag/AgCl, and Hg/HgO. By using the screen printing technique, the above electrode material can be easily manufactured onto the plate.

Insulating membrane (2) is formed onto the electrode material (3) layer excluding electrode site and electrode connection part (1).

Meanwhile, preferably the distance between the junction site and the working electrode of the planar reference electrode is relatively long when used in potentiometry, and shorter when used in voltammetry to reduce the IR drop problem.

Furthermore, the present invention also provides processes for preparing the planar reference electrode.

Particularly, in the case that the junction of the planar reference electrode is composed of porous material or capillary type, the process for fabricating the planar reference electrode comprises 7 stages as follows;

(1) forming electrode connection part (1) on plate (4);
(2) forming electrode (3) on plate (4) by using the screen printing method;
(3) forming insulating membrane (2) layer by screen printing onto the conductors (3) formed at step 2, excluding electrode site, capillary channel and connection sites;
(4) forming insoluble metal salt layer on the electrode site;
(5) placing a thin film that can provide a well around the electrode site and a capillary onto the substrate;
(6) placing inner reference solution (5) within the well;
(7) forming protection membrane layer (8) that cover the inner reference solution; and In the case that the junction of the planar reference electrode is composed of porous polymer membrane, the process for preparing comprises 6 stages as follows;

(1) forming electrode connection part (1) on plate (4);
(2) forming electrodes (3) on plate (4) by using the screen printing method;
(3) forming insulating membrane (2) layer by screen printing onto the conductors (3) formed at step 2, excluding electrode site and connection sites (1);
(4) forming insoluble metal salt layer onto the electrode;
(5) forming hydrogel layer (5) using soluble polymer containing highly concentrated electrolyte; and
(6) forming porous polymer protection membrane (9) on the hydrogel layer using porous polymer covering hydrogel layer completely.

At stage (6), porous polymer protection membrane (9) is made to cover the entire hydrogel layer and then blocked direct contact with sample.

Meanwhile, in the case that electrode material consists of metal layer/insoluble metal layer, the metal layer is formed by using the screen printing method and then insoluble metal salt layer can be built by using separate processes. For example, in the case that electrode material (3) is metal Ag and insoluble metal salt AgCl, insoluble metal layer can be formed by using the chemical reaction with $FeCl_3$ or $KCrO_3Cl$ solution. Also, the insoluble metal salt can be overlaid within solution containing $Cl^-$ ion such as HCl, in which constant current (for example 0.4 mA/cm) is used to electroplate the layer for several minutes.

The planar reference electrode of the present invention is insensitive toward the changes in $Cl^-$, $Na^+$, and $H^+$ concentration in solution, and exhibits a short activation period, typically less than a few minutes. The electric potential is maintained stable for more than 4000 seconds; when the $K^+$, $Na^+$, $NH_4^+$, $H^+$, and $Cl^-$ selective electrodes are referenced to the planar reference electrode of present invention, they all exhibit the same potentiometric responses as they are referenced to the conventional reference electrodes.

Cyclic voltammetry for the ferri/ferrocyanide redox reaction with respect to the planar reference electrode result in a similar curve obtained with the calomel electrode. Thus the planar reference electrode of the present invention can be used not only in the potentiometry but also in the voltammetry.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1
Preparation 1 of the Planar Reference Electrode

The reference electrode of the present invention was prepared according to the method described below by using porous cotton thread as junction material.

First, electric conducting line was built onto the polyester plate (4) by using the conventional screen printing method with silver paste from the region of electrode site (3) and electrode connection part (1). Then insulating membrane (2) layer onto the metal conductor (3) excluding the electrode site and electrode connection part (1) was formed by using the typical screen printing method employing an insulating paste.

The above electrode (3) was placed in 0.0175 M concentration of $FCl_3$ solution for 20–30 minutes to form insoluble metal salt layer, AgCl, onto the electrode site (3).

The polyester was cut out in a size that can cover the electrode site and then punched to form a well (6 mm diameter) that can hold inner reference solution. From one end of the well to the outer boundary, a straight channel was made to place a junction material.

Porous cotton thread was utilized as junction material and placed on the straight channel of the polyester film. The polyester layer (8) prepared above was glued to the plate (4).

Inner reference solution (5) was made by the following process; preparing 98.5 weight % of glycerol solution and saturated with KCl. And 3 µl of the inner reference solution was put into the well formed with the polyester layer.

Finally, another polyester film (3) that serves as the outer protection membrane was glued on the top of the well containing polyester (8), which completes the construction of the reference electrode as shown in FIG. 1.

Example 2
Preparation 2 of the Planar Reference Electrode

The reference electrode was prepared according to the method as described in example 1 by using porous glass fiber (Whatman international Ltd., Maidstone, England) as junction material instead of cotton thread.

Example 3
Preparation 3 of the Planar Reference Electrode

The reference electrode was prepared according to the method as described in example 1 by using porous cellulose nitrate (Whatman international Ltd., Maidstone, England) as junction material instead of cotton thread.

Example 4
Preparation 4 of the Planar Reference Electrode

The reference electrode with capillary type junction was prepared as described below.

The electrode comprising metal layer and insoluble matal layer, electrode connection and insulating membrane was made by using the process as described in example 1.

The polyester was cut out in a size that can cover the electrode site and then punched to form a well (6 mm diameter) that can hold inner reference solution. From one end of the well to outer boundary, a straight channel was made by simply cutting a line with sharp blade to form a capillary.

Inner reference solution (5) was made by the following process; preparing 85 weight % of glycerol solution and 3 M of KCl solution and mixing with 2:1 volume ratio. And 3 µl of the inner reference solution was put into the well formed by the polyester layer. Finally, the another polyester film (3) that serves as the outer protection membrane was glued on the top of the well containing polyester (8), which completes the construction of the reference electrode as shown in FIG. 1.

Example 5
Preparation 5 of the Planar Reference Electrode

The reference electrode was prepared according to the method as described in example 4 by using capillary type junction. But, Ag was utilized as electrode material instead of forming Ag/AgCl layer and 85 wt % of glycerol solution saturated with $AgNO_3$ as an inner reference solution.

Example 6
Preparation 6 of the Planar Reference Electrode

The reference electrode was prepared according to the method as described in example 4 by using capillary type junction. But polymeric glue saturated with KCl was utilized as an inner reference solution.

Example 7
Preparation 7 of the Planar Reference Electrode

The reference electrode was prepared according to the method described in example 4 by using capillary type junction. But Ag was utilized as the electrode instead of Ag/AgCl and a polymeric glue saturated with AgNO$_3$ as an inner reference solution.

Example 8
Preparation 8 of the Planar Reference Electrode

The reference electrode with porous polymer membrane as the outer protection membrane, which also serves as a junction, was prepared as described below.

The electrode comprising metal layer and insoluble metal layer, electrode connection and insulating membrane was built onto a polycarbonate plate by using the process described in example 1.

Soluble polymer PVP (poly(vinyl pyrrolidone)) was dissolved in 2 M KCl solution (2 wt %) and then 0.2 M CaCl$_2$ was added to this solution. The above solution was mounted onto the reference electrode site by using an air press-type dispenser and dried at 60° C. for 30 minutes, forming hydrogel layer containing electrolytes of high concentration on Ag/AgCl electrode.

90 mg of porous polymer, cellulose nitrate (NC), was dissolved in 1000 μl of organic solvent THF (tetrahydrofuran). NC solution was dispensed onto the hydrogel layer by using an air-press type dispenser and dried at 60° C. for 30 minutes.

By the process described above, hydrogel layer containing electrolytes with high concentration onto Ag/AgCl electrode and porous polymer protection membrane, cellulose nitrate membrane, were made and the planar reference electrode was completed (as shown in FIG. 2).

Table 1 shows the composition of components and junction type of the planar reference electrode as prepared in the example 1–example 8.

TABLE 1

Composition of the planar reference electrode

| example | electrode | junction type | junction material | inner reference solution | plate/ protection membrane |
|---|---|---|---|---|---|
| 1 | Ag/AgCl | porous material | cotton thread | 98.5 weight % of glycerol solution saturated with KCl | polyester |
| 2 | Ag/AgCl | porous material | glass fiber | 98.5 weight % of glycerol solution saturated with KCl | polyester |
| 3 | Ag/AgCl | porous material | cellulose nitrate | 98.5 weight % of glycerol solution saturated with KCl | polyester |
| 4 | Ag/AgCl | capillary | no | 98.5 weight % of glycerol solution saturated with KCl | polyester |
| 5 | Ag | capillary | no | 98.5 weight % of glycerol solution | polyester |
| 6 | Ag/AgCl | capillary | no | liquid pool saturated with AgNO$_3$ | polyester |
| 7 | Ag | capillary | no | liquid pool saturated with KCl liquid pool saturated with AgNO$_3$ | polyester |
| 8 | Ag/AgCl | porous polymer membrane | cellulose nitrate membrane | hydrogel of 2 weight % PVP, 0.2M CaCl$_2$, 2M KCl | poly-carbonate/ cellulose nitrate membrane |

Figure 3:
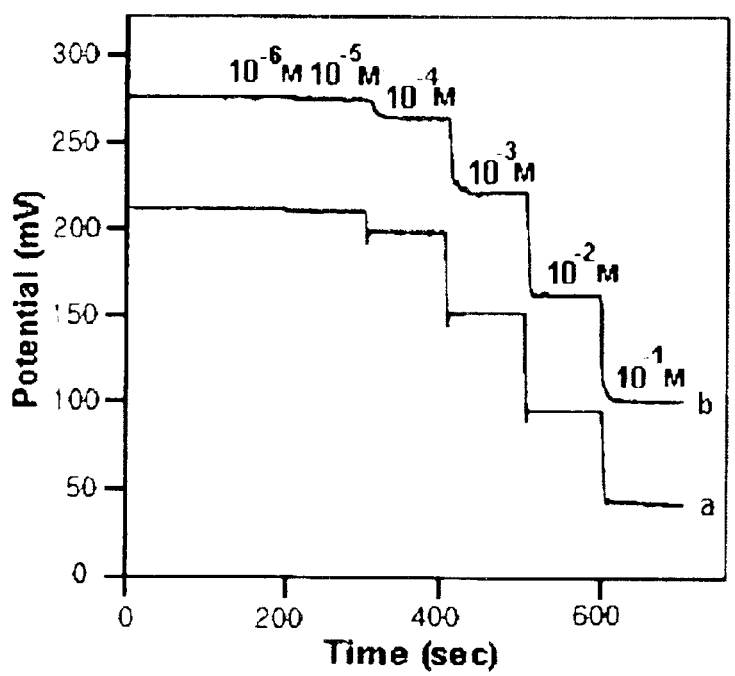
FIG. 3 shows the graph of potentiometric response curve of Ag/AgCl electrode to $Cl^-$.

Experimental Example 1
Electrochemical Performance of the Planar Reference Electrode with Ag/AgCl Electrode—Sensitivity Toward Cl$^-$ Ion We have performed the experiment described below in order to examine the performance of the planar reference electrode prepared in example 1–4, 6 and 8. As shown in FIG. 3., The bare Ag/AgCl electrode formed on the substrate exhibited proper sensitivity to 10$^{-6}$–10$^{-1}$ M Cl$^-$ ion. To examine the performance of the Ag/AgCl electrodes, their potential responses with respect to the conventional type reference electrode, Orion® sleeve-type double junction reference electrode (Ag/AgCl electrode, 90-20 (USA, ORION corp.) was measured.

The Ag/AgCl electrodes which was prepared as described in example 1–4 and 6 result in the 53.03 mV/dec of slope to Cl$^-$ ion. And the electrode which was prepared as described in example 8 exhibited 54.6 mV/dec of slope to Cl$^-$ ion. The responses of Ag/AgCl electrode may be explained with the following equations:

$$AgCl + e^- \rightarrow Ag + Cl^-$$

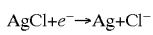

$$E = E_{Ag/AgCl} - (2.303 RT/F) \log a_{Cl^-}$$

E: electric potential
$E_{Ag/AgCl}$: standard potential of Ag/AgCl
R: gas constant
T: absolute temperature
F: Faraday constant
$a_{Cl^-}$: activity of Cl$^-$ In both cases, the response slopes, 53.03 mV/dec and 54.60 mV/dec, to Cl$^-$ are close to that of the theoretical one, 59.16 mV/dec at the given room temperature.

Experimental Example 2
Electrochemical Performance of the Planar Reference Electrode—Sensitivity Toward pH To examine the performance of the planar reference electrodes of the present invention, their potential responses with respect to the conventional type reference electrode, Orion® sleeve-type double junction reference electrode (Ag/AgCl electrode, 90-20(USA, ORION corp.) was measured in varying pH condition. The results are shown in FIG. 4.

Figure 4:
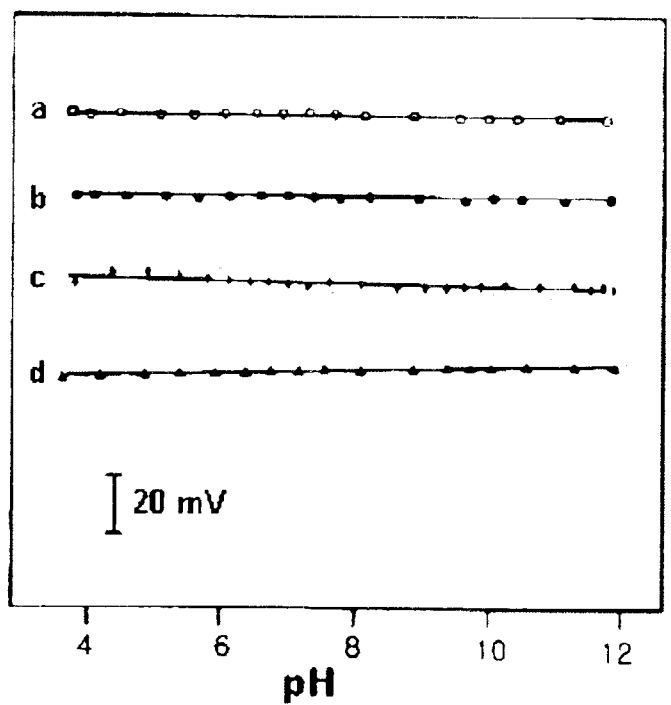
FIG. 4 shows the pH response of the planar reference electrode of the present invention employing, a: the planar reference electrode of example 1 (junction: cotton thread; inner reference solution: 98.5% glycerol solution of saturated NaCl), b: the planar reference electrode of example 4 (junction: capillary type; inner reference solution: 85% glycerol with 3 M KCl (volume ratio; 2:1)), c: the planar reference electrode of example 6 (junction: capillary type; inner reference solution: polymeric glue saturated with KCl), d: the planar reference electrode of example 8 (junction: cellulose nitrate membrane; inner reference solution: PVP (polyvinyl pyrrolidone) polymer hydrogel prepared by using 2 M KCl solution dissolved in 0.2 M $CaCl_2$).

As shown in FIG. 4, all planar reference electrodes of the present invention exhibited insensitive responses to varying hydrogen ion concentration in the pH 3–12 range.

Experimental Example 3
Electrochemical Performance of the Planar Reference Electrode—Sensitivity Toward NaCl To examine the performance of the planar reference electrodes of the present invention, their potential responses with respect to the conventional type reference electrode, Orion® sleeve-type double junction reference electrode (Ag/AgCl electrode, 90-20 (USA, ORION corp.) was measured in varying NaCl concentration. The results are shown in FIG. 5.

Figure 5:
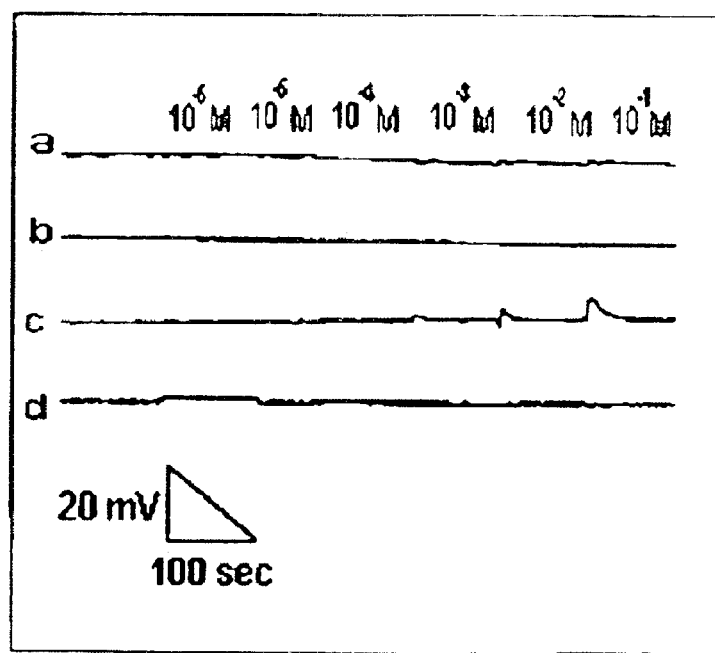
FIG. 5 shows the response of the planar reference electrode to the change in $Cl^-$ ion concentration employing, a: the planar reference electrode of example 1, b: the planar reference electrode of example 4, c: the planar reference electrode of example 6, d: the planar reference electrode of example 8.

As shown in FIG. 5, all planar reference electrodes of the present invention exhibited insensitive responses to varying Cl⁻ ion concentration in the $10^{-1}$–$10^{-6}$ range.

Experimental Example 4
Electrochemical Performance of the Planar Reference Electrode—Activation Period We have performed the experiment to examine the activation period of the planar reference electrodes as described below.

The same electrode system with that of the above experimental example 2 was used to measure the activation period of the reference electrodes by immersing them in 0.002 M of Tris-$H_2SO_4$ buffer solution of pH 7.4.

Figure 6:
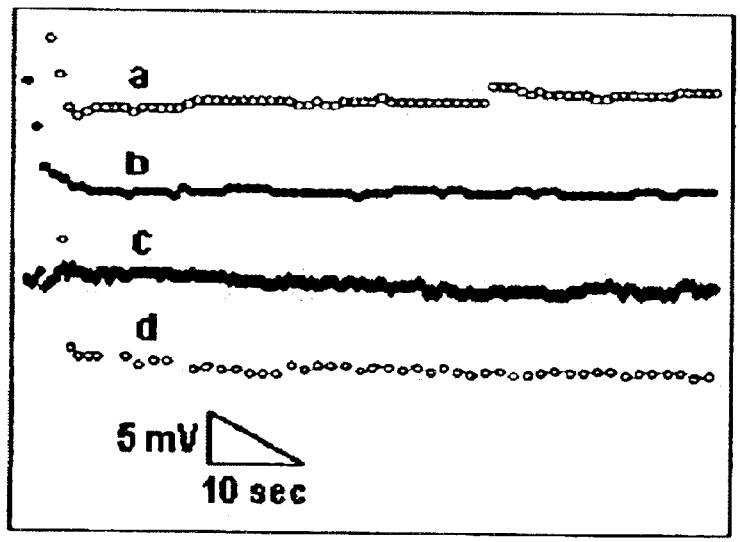
FIG. 6 shows the activation period of the planar reference electrode of the present invention employing, a: the planar reference electrode of example 1, b: the planar reference electrode of example 4, c: the planar reference electrode of example 6, d: the planar reference electrode of example 8.

As shown in FIG. 6, the planar reference electrode using porous material as junction were stabilized less than 10 seconds of activation (FIG. 6a). The electrodes described in example 1–3, those employing porous junction material, showed similar results. In addition, the capillary-type planar reference electrodes (example 4, 6; FIG. 6b, FIG. 6c) and the planar reference electrode with porous polymer membrane (example 8; FIG. 6d) were also activated less than several seconds.

As described above, the planar reference electrodes of the present invention are suitable to use in clinical and industrial fields, as they require very short activation time within several seconds.

Experimental Example 5
Electrochemical Performance of the Planar Reference Electrode—Stability In order to see that the planar reference electrode maintains stable electrochemical property for an extended period of time, we have examined their stability as described below.

The same electrode systems described in example 2 was used and the planar reference electrodes, and they were immersed in 0.002 M Tris-$H_2SO_4$ buffer solution (pH 7.4) to measure the electric potential variation for more than 4000 seconds.

Figure 7:
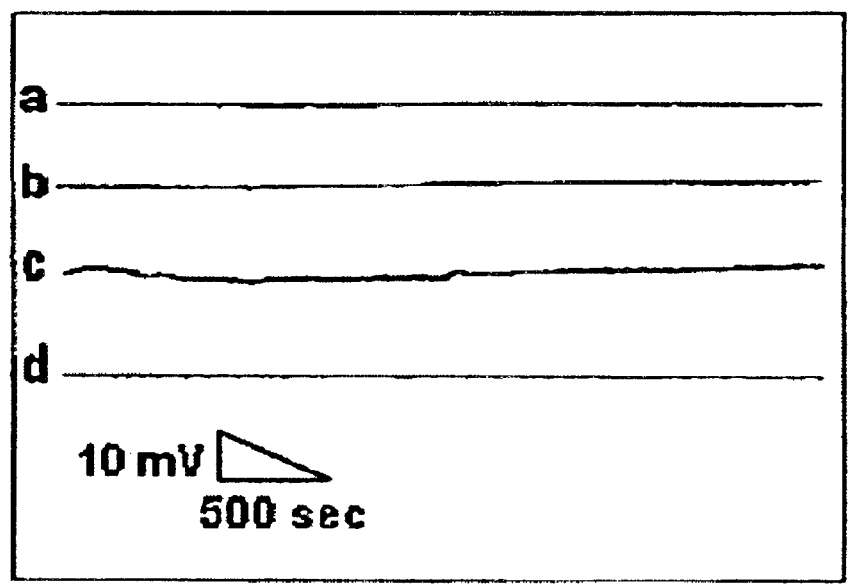
FIG. 7 shows the potential stability of the planar reference electrode of the present invention with time employing, a: the planar reference electrode of example 1, b: the planar reference electrode of example 4, c: the planar reference electrode of example 6, d: the planar reference electrode of example 8.

As shown in FIG. 7, the planar reference electrode using porous material as junction maintained stable electric potentials for more than 4000 seconds (FIG. 7a). The electrodes described in example 1–3, those employing porous junction material, showed similar results. In addition, the capillary-type planar reference electrodes (example 4, 6; FIG. 7b, FIG. 7c) and the planar reference electrode with porous polymer membrane (example 8) were also maintained stable for more than 4000 seconds.

Experimental Example 6
Comparative Experiment for the Performance of Conventional Reference Electrode and the Planar Reference Electrodes of the Present Invention—Sensitivity Toward Cl ion In order to compare the potentiometric performance of the planar reference electrode of the present invention with that of the conventional reference electrode, we have performed the experiment as described below.

The potentiometry electrode system was composed of working electrode (typical Ag/AgCl electrode), reference electrodes (the planar reference electrode of the present invention and conventional planar reference electrode) and volt meter which can measure the potential differences between the working electrode and conventional reference, and between the working and the planar reference electrode. Standard solutions ($10^{-6}$–$10^{-1}$ M of NaCl solutions) were used to examine the response characteristics toward Cl⁻ ion. The results were depicted in FIG. 8 and listed in Table 2.

TABLE 2

Sensitivity toward Cl ion

| reference electrode | sensitivity toward Cl ion of working electrode (mV/dec) |
|---|---|
| Conventional reference | 53.02 |
| Example 1 | 54.88 |
| Example 2 | 54.13 |
| Example 3 | 53.39 |
| Example 4 | 59.20 |
| Example 5 | 54.61 |
| Example 6 | 52.79 |

Figure 8:
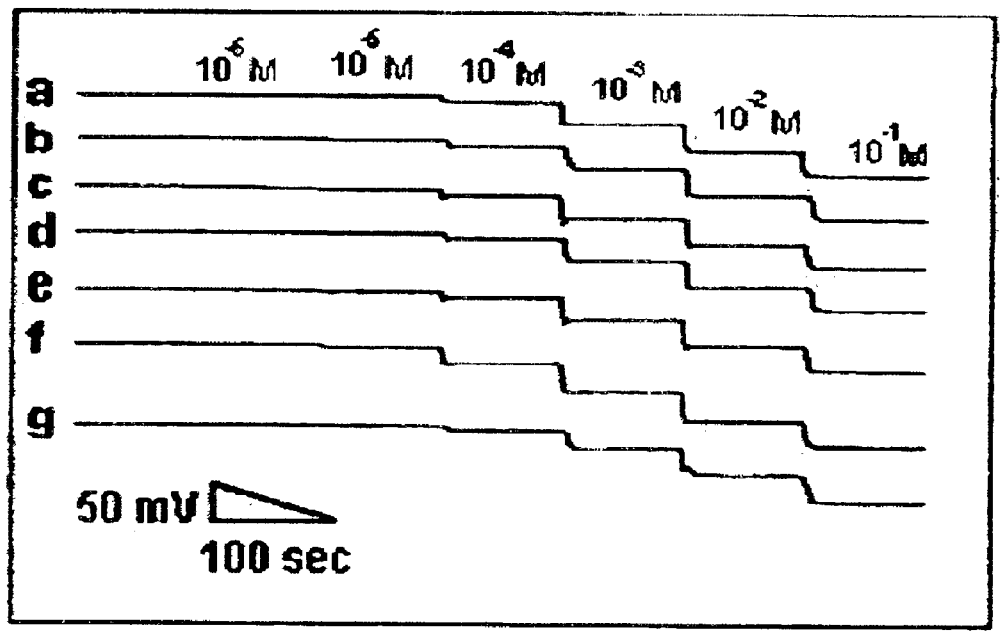
FIG. 8 shows the $Cl^-$ ion response of the Ag/AgCl working electrode with respect to the conventional reference electrode and the planar reference electrode of the present invention employing, a: the conventional reference electrode (Orion sleeve-type double junction), b: the planar reference electrode of example 1, c: the planar reference electrode of example 2 (junction: glass fiber; inner reference solution: 98.5% glycerol solution of saturated NaCl), d: the planar reference electrode of example 3 (junction: cellulose nitrate; inner reference solution: 98.5% glycerol solution of saturated NaCl), e: the planar reference electrode of example 4, f: the planar reference electrode of example 6, g: the planar reference electrode of example 8.

As shown in FIG. 8 and table 2, Ag/AgCl working electrode exhibited 53.02 mV/dec of slope to Cl⁻ ion (FIG. 8a) with respect to the conventional reference electrode. With respect to the planar reference electrodes of the present invention, i.e., the reference electrodes prepared in example 1, 2, 3, 4, 6 and 8, the working electrode exhibited 54.88 mV/dec of slope toward Cl⁻ ion (example 1, FIG. 8b), 54.13 mV/dec (example 2, FIG. 8c), 53.39 mV/dec (example 3, FIG. 8d), 59.20 mV/dec (example 4, FIG. 8e), 54.61 mV/dec (example 6, FIG. 8f) and 52.79 mV/dec (example 8, FIG. 8g). These results are essentially the same as that observed with the conventional reference electrode system.

Experimental Example 7
Comparative Experiment for the Performance of Conventional Reference Electrode and the Planar Reference Electrode of the Present Invention—Sensitivity Toward H ion (pH)

As described in experimental example 6, similar experiments were carried out to examine the potentiometric performance of the planar reference electrodes of the present invention. Hydrogen ion-selective electrode was prepared with the membrane doped with tridodecylamine (TDDA) on the planar-format electrode. The comparative potentiometric responses of the H⁺-selective electrode with respect to the conventional electrode and planar reference electrodes were shown in FIG. 9.

Figure 9:
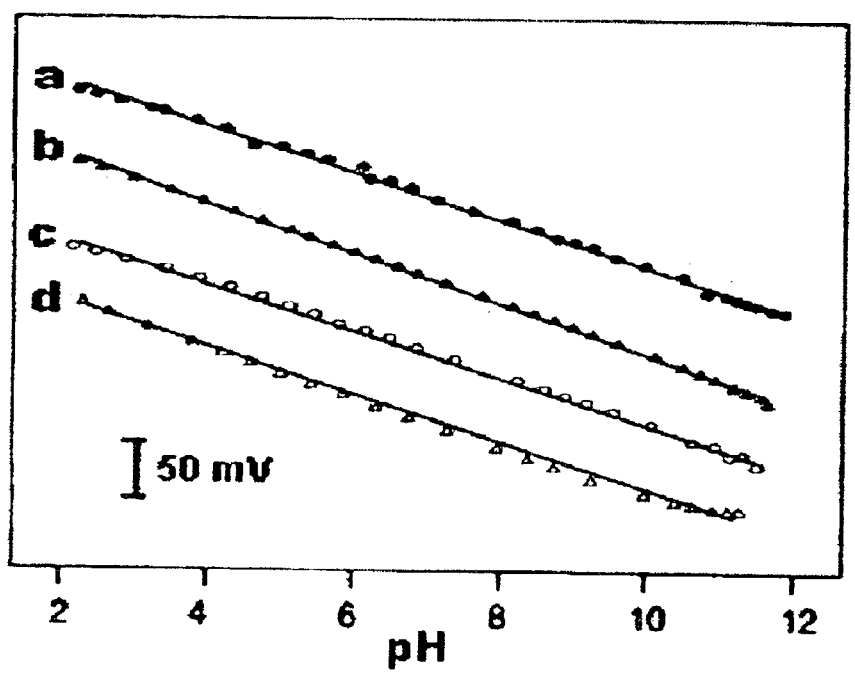
FIG. 9 shows the hydrogen ion response of hydrogen ion-selective solid-state type working electrode with respect to the conventional reference electrode and the planar reference electrode of the present invention employing, a: the conventional type reference electrode, b: the planar reference electrode of example 4, c: the planar reference electrode of example 6, d: the planar reference electrode of example 8.

As depicted in FIG. 9, the slope toward H⁺ ion was 53.59 mV/dec with respect to the conventional reference electrode (FIG. 9a). With respect to the reference electrode of the present invention, the reference electrode prepared in example 4 showed 54.23 mV/dec of slope (FIG. 9b), the reference electrode prepared in example 9, 58.10 mV/dec (FIG. 9c), the reference electrode prepared in example 8, 57.58 mV/dec (FIG. 9d). They exhibited essentially the same response characteristics compared to that of the conventional reference electrode.

Experimental Example 8
Comparative Experiment for the Performance of Conventional Reference Electrode and the Planar Reference Electrode of the Present Invention—Sensitivity Toward Na⁺ ion As described in experimental example 6, similar experiments were carried out to examine the potentiometric performance of the planar reference electrodes of the present invention. Hydrogen ion-selective electrode was prepared with the membrane doped with 4-tertbutylcalix(4)arene on the planar-format electrode. The comparative potentiometric responses of the $H^+$-selective electrode with respect to the conventional electrode and planar reference electrodes were shown in FIG. 10.

Figure 10:
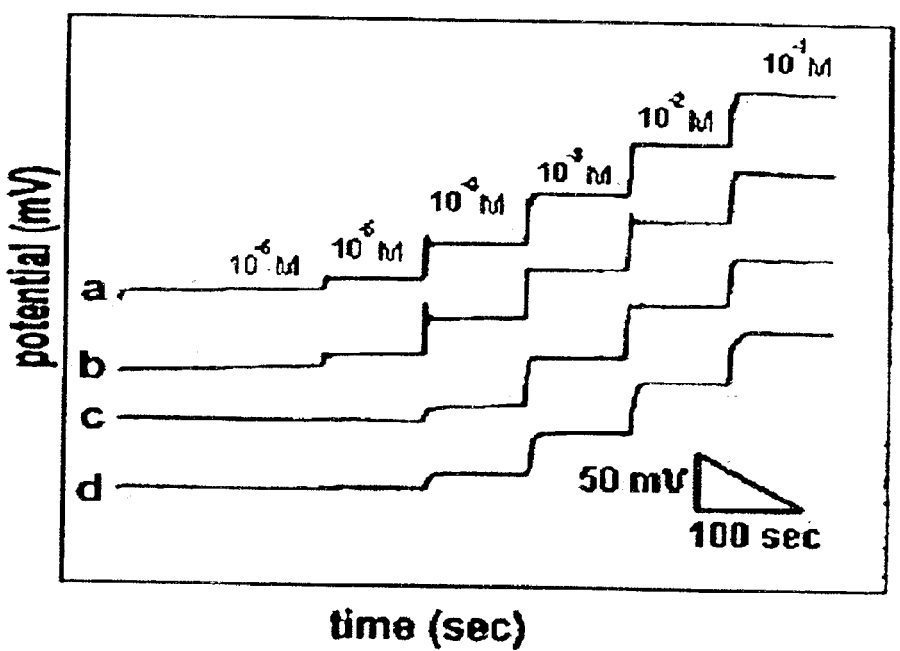
FIG. 10 shows the sodium ion response of $Na^+$ ion-selective solid-state type working electrode with respect to the conventional type reference electrode and the planar reference electrode of the present invention employing, a: the conventional type reference electrode, b: the planar reference electrode of example 4, c: the planar reference electrode of example 6, d: the planar reference electrode of example 8.

As shown in FIG. 10, the response slope toward $Na^+$ ion was 57.18 mV/dec with respect to the conventional reference electrode (FIG. 10a). With respect to the planar reference electrodes of the present invention, the reference electrode prepared in example 4 showed 59.72 mV/dec of slope (FIG. 10b), the reference electrode prepared in example 6, 57.28 mV/dec (FIG. 10c), the reference electrode prepared in example 8, 56.21 mV/dec (FIG. 10d). They exhibited essentially the same response characteristics compared to that of the conventional reference electrode.

Experimental Example 9

Comparative Experiment for the Performance of conventional Reference Electrode and the Planar Reference Electrode of the Present Invention—Sensitivity Toward $K^+$ ion As described in experimental example 6, similar experiments were carried out to examine the potentiometric performance of the planar reference electrodes of the present invention. Hydrogen ion-selective electrode was prepared with the membrane doped with valinomycin on the planar-format electrode. The comparative potentiometric responses of the $H^+$-selective electrode with respect to the conventional electrode and planar reference electrodes were shown in FIG. 11.

Figure 11:
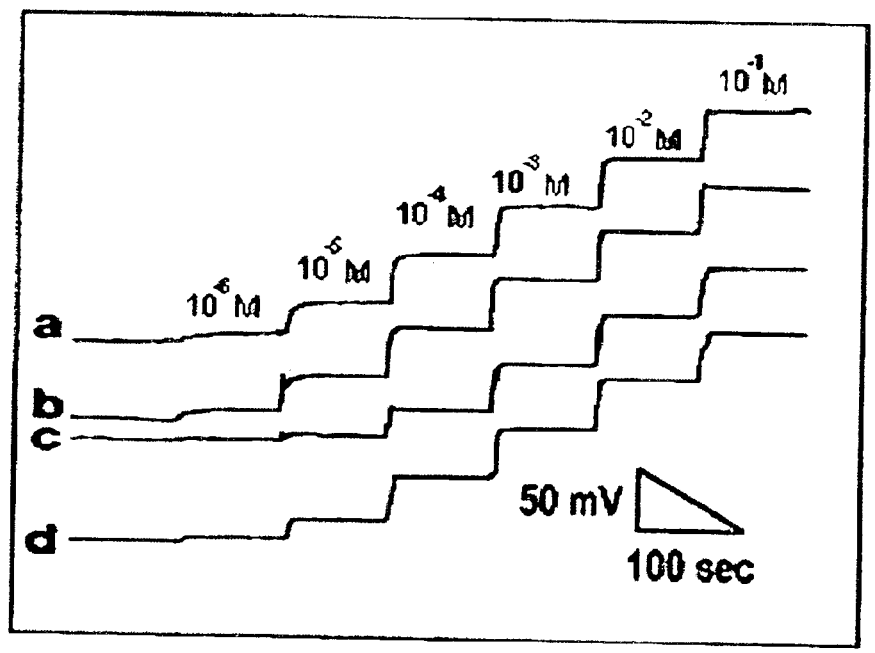
FIG. 11 shows the calcium ion response of $Ca^{2+}$ ion-selective solid-state type working electrode with respect to the conventional type reference electrode and the planar reference electrode of the present invention employing, a: the conventional type reference electrode, b: the planar reference electrode of example 5, (junction: capillary type; inner reference solution: 85% glycerol solution of saturated $AgNO_3$), c: the planar reference electrode of example 7 (junction: capillary type; inner reference solution: polymer glue of saturated $AgNO_3$), d: the planar reference electrode of example 8.

As shown in FIG. 11, the response slope toward $K^+$ ion was 57.04 mV/dec with respect to the conventional reference electrode (FIG. 11a). With respect to the reference electrode of the present invention, the reference electrode prepared in example 5 showed 55.10 mV/dec of slope (FIG. 11b), the reference electrode prepared in example 7, 55.74 mV/dec (FIG. 11c), the reference electrode prepared in example 8, 56.70 mV/dec (FIG. 11d). They exhibited essentially the same response characteristics compared to that of the conventional reference electrode.

Experimental Example 10

Sensitivity Toward Urea and Ammonium ion

In order to examine the sensitivity of the working electrode toward urea and ammonium with respect to the planar reference electrode of the present invention, we have performed the experiment as described below.

Ammonium ion-selective electrode was fabricated with nonactin-doped polymer membrane on the planar electrode. Urea responsive electrode was prepared by immobilizing urease on the top of the ammonium-selective membrane. Experimental setup was similar to that described in experimental example 6. The results are shown in FIG. 12.

Figure 12:
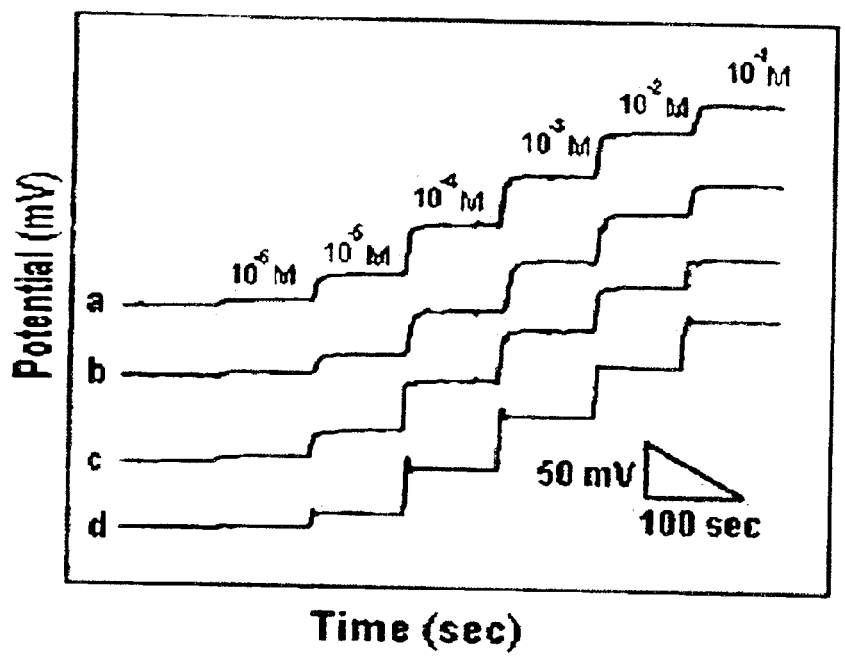
FIG. 12 shows the urea and ammonium ion response of urea and ammonium ion-selective solid-state type working electrode with respect to the planar reference electrode of the present invention, a: urea response with the planar reference electrode of example 4, b: ammonium response with the planar reference electrode of example 4, c: urea response with the planar reference electrode of example 8, d: ammonium response with the planar reference electrode of example 8.

As shown in FIG. 12, the response slope toward urea was 56.2 mV/dec with respect to the reference electrode of example 4 (FIG. 12a). The slope toward ammonium was 55.6 mV/dec (FIG. 12b). The slope toward urea was 56.2 mV/dec with respect to the planar reference electrode of example 8 (FIG. 12c) and the slope toward ammonium was 56.2 mV/dec (FIG. 12d). Thus the planar reference electrode of the present invention was is a proper reference electrode system in the measurement of ammonium and urea.

Experimental Example 11

Cyclic Voltammetry (CV) Curve for the Feeri/Ferrocyanide Redox Reaction

In order to examine the usefulness of the planar reference electrode of the present invention in voltammetry, we examined the CV for the ferri/ferrocyanide redox reaction employing the planar reference electrode of the present invention.

The voltametry electrode system was composed of working electrode, supporting electrode, reference electrode and current or potentiostat, which can measure the electric charge. The conventional type reference electrode, saturated calomel electrode was used as a reference electrode to compare with the planar reference electrode of the present invention prepared in example 4, and the carbon paste electrode as a working electrode and Pt electrode as a supporting electrode. The electrode of the above 3 electrode system was immersed in 1 mM of $K_3Fe(CN)_6$ solution to obtain CV for the oxidation-reduction pair of $K_3Fe(CN)_6^{3-}$/$K_3Fe(CN)_6^{2-}$. The results were shown in FIG. 13.

Figure 13:
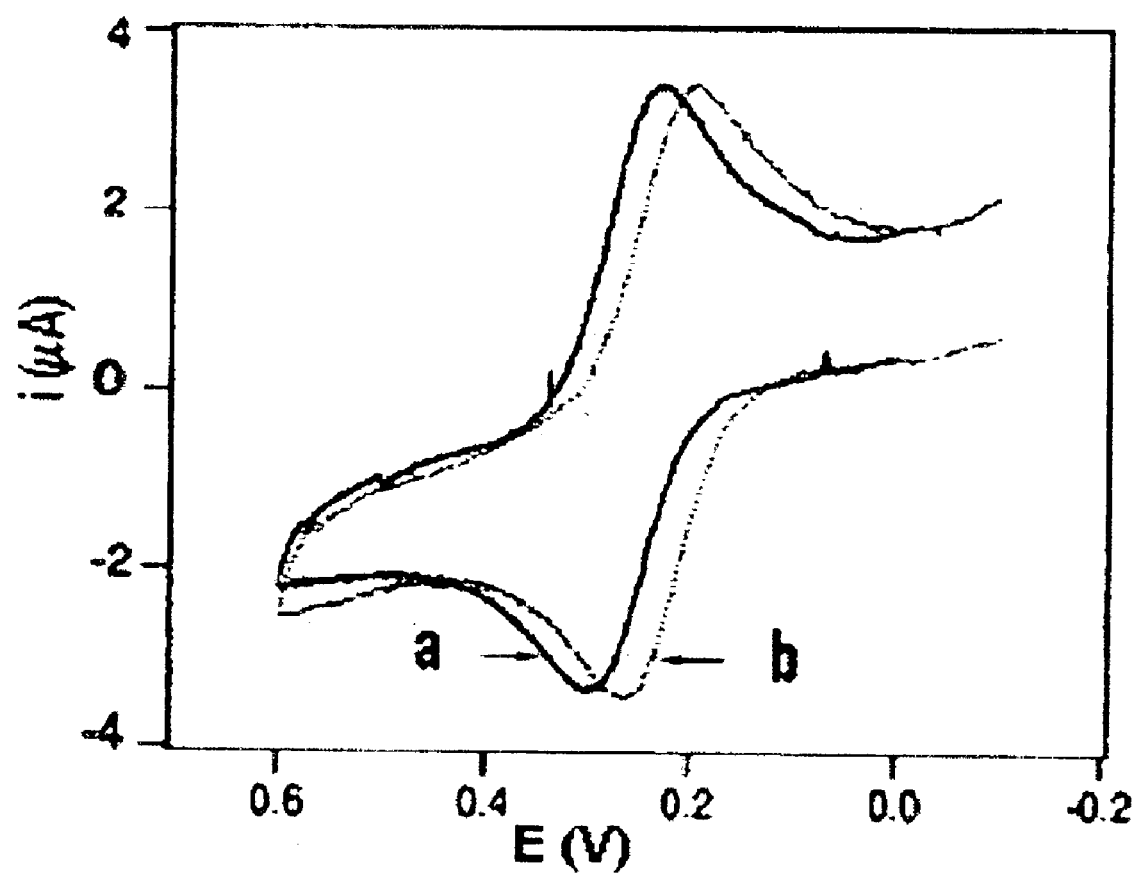
FIG. 13 shows the voltage-current response curve of the screen-printed carbon paste electrode to ferri/ferrocyanide redox reaction with respect to the planar reference electrode of the present invention and the saturated calomel electrode employing, a: the planar reference electrode of example 4, b: conventional saturated calomel electrode.

As shown in FIG. 13, the potential difference between the oxidation and reduction peaks was 65 mV (FIG. 13a) when the planar reference electrode of the present invention was used. When the conventional saturated calomel reference electrode was used, the potential difference between the oxidation and reduction peaks was also 65 mV (FIG. 13b), which was the same value as that obtained with the planar reference electrode of the present invention. In addition, maximum oxidation and maximum reduction currents were also identical in the above 2 cases using different reference electrodes, respectively. However, in the CV of the ferri/ferrocyanide system with the planar reference electrode, the electric potential of the maximum oxidation peak and the maximum reduction peak were shifted toward positive direction of about 20 mV compared to those observed with the conventional saturated calomel reference electrode. This difference is related to the difference in standard potential of the respective reference electrodes, but not in their functions.

As stated above, the planar reference electrode of the present invention was identified to have the same performance with that of the calomel reference electrode and thus can be exploited as a reference electrode system in voltammetry.

INDUSTRIAL APPLICABILITY

The planar reference electrode of the present invention has the junction which is composed of porous material such as cotton thread, glass fiber, cellulose nitrate, cellulose acetate, filter paper and any other material that can induce capillary action; porous polymer membrane; or a capillary embedded in the assembly. The planar reference electrodes of the present invention provide stable electric potential and short activation period, and the reproducibility of the results was outstanding.

In addition, the planar reference electrodes of the present invention have simpler structure than the existing reference electrodes, and can be prepared conveniently. Furthermore, it can be produced cheaply in mass production, and used in both potentiometry and voltammetry. Electrode material and inner reference solution of the planar reference electrode may be changed to the demand of analytical purpose. Therefore, the scope of the planar reference electrode of the present invention is not limited only to the examples described in this document.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A planar reference electrode comprising: a plate; an electrode connecting part; an electrode; an insulating membrane; an inner reference solution; a porous polymer membrane which functions as both a junction and a protection membrane, wherein porous polymer is dissolved in the organic solvent to form porous polymer solution and the porous polymer solution is dispensed onto the inner reference solution to form the porous polymer membrane, wherein the plate is formed of a material partially soluble in the organic solvent to make the porous polymer membrane directly fixed to the plate, wherein the inner reference solution is an electrolyte selected from the group consisting of 85–99 weight % of glycerol solution, 1–10 weight % of agar solution, polymeric glue, and water soluble polymers.

2. The planar reference electrode as set forth in claim 1, wherein the porous polymer membrane is formed of cellulose nitrate.

3. The planar reference electrode as set forth in claim 1, wherein the plate is polycarbonate.

4. The planar reference electrode as set forth in claim 1, wherein the electrode is selected from the group consisting of Ag, Pd, Cu, Pt, Ag/AgCl, Ag containing 1–5 weight % of Pd and Ag coated with Nafion.

5. The planar reference electrode as set forth in claim 1, wherein the electrolyte is $AgNO_3$ or perchloric acid for an Ag electrode, KCl or NaCl for an Ag/AgCl electrode, and KOH or NaOH for a mercury/mercury oxide electrode.

6. A method for fabricating the planar reference electrode of claim 1 which comprises:
   (1) forming the electrode connecting part on the plate;
   (2) forming the electrode on the plate by using a screen printing method;
   (3) forming the insulating layer by screening printing on the electrode, to provide a well around the electrode;
   (4) placing the inner reference solution within the well; and
   (5) forming the porous protection membrane to cover the inner reference solution.

7. A planar reference electrode comprising: a plate; an electrode connecting part; an electrode; an insulating membrane; an inner reference solution; a junction; and a non-porous protection membrane, wherein the junction is formed in a line of micro capillary, the line of micro capillary being formed as a vacancy within the insulating membrane by making the vacancy in forming the insulating membrane, wherein the inner reference solution is an electrolyte selected from the group consisting of 85–99 weight % of glycerol solution, 1–10 weight % of agar solution, polymeric glue, and water soluble polymers.

8. The planar reference electrode as set forth in claim 7, wherein the plate is selected from the group consisting of alumina, glass and plastic substance.

9. The planar reference electrode as set forth in claim 7, wherein the electrode is selected from the group consisting of Ag, Pd, Cu, Pt, Ag/AgCl, Ag containing 1–5 weight % of Pd and Ag coated with Nafion.

10. The planar reference electrode as set forth in claim 7, wherein the electrolyte is $AgNO_3$ or perchloric acid for a Ag electrode, KCl or NaCl for a Ag/AgCl electrode, and KOH or NaOH for a mercury/mercury oxide electrode.

11. The planar reference electrode as set forth in claim 7, wherein the non-porous protection membrane is formed by polyester.

12. A method for fabricating the planar reference electrode of claim 7 which comprises:
   (1) forming the electrode connecting part on the plate;
   (2) forming the electrode on the plate by using a screen printing method;
   (3) forming the insulating layer by screen printing on the electrode, to provide a well around the electrode and the line of micro capillary;
   (4) placing the inner reference solution within the well; and
   (5) forming the non-porous protection membrane to cover the inner reference solution.

* * * * *